(12) United States Patent
Woo

(10) Patent No.: US 7,578,842 B2
(45) Date of Patent: Aug. 25, 2009

(54) PROSTHETIC HEART VALVES

(75) Inventor: Yi-Ren Woo, Woodbury, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 220 days.

(21) Appl. No.: 11/542,903

(22) Filed: Oct. 3, 2006

(65) Prior Publication Data

US 2008/0082163 A1    Apr. 3, 2008

(51) Int. Cl.
*A61F 2/24*    (2006.01)
(52) U.S. Cl. .................................................. 623/2.1
(58) Field of Classification Search ............... 623/2.41, 623/2.1
See application file for complete search history.

(56) References Cited

U.S. PATENT DOCUMENTS

| | | | |
|---|---|---|---|
| 6,074,417 A * | 6/2000 | Peredo | 623/2.1 |
| 6,458,156 B1 | 10/2002 | Wan et al. | |
| 7,172,625 B2 * | 2/2007 | Shu et al. | 623/2.41 |
| 7,320,704 B2 * | 1/2008 | Lashinski et al. | 623/2.11 |
| 2002/0115985 A1 | 8/2002 | Larsen et al. | |
| 2002/0151968 A1 * | 10/2002 | Zilla et al. | 623/1.39 |
| 2003/0083741 A1 | 5/2003 | Woo et al. | |
| 2004/0093080 A1 | 5/2004 | Helmus et al. | |
| 2005/0191331 A1 | 9/2005 | Hunter et al. | |

FOREIGN PATENT DOCUMENTS

WO    WO 96/30060    10/1996
WO    WO 97/15245    5/1997

* cited by examiner

*Primary Examiner*—Suzette J Gherbi
(74) *Attorney, Agent, or Firm*—Lerner, David, Littenberg, Krumholz & Mentlik, LLP

(57) ABSTRACT

A prosthetic heart valve includes a hydrogel material in its sewing cuff. The hydrogel material may be accompanied by an anticoagulant. If the hydrogel (and/or any included anticoagulant) might react with a packaging solution in which the valve is stored after inclusion of the hydrogel (and any anticoagulant), the hydrogel (and any anticoagulant) may be included in a protective but deliberately frangible pouch in the sewing cuff. After the valve is out of the packaging solution, the pouch can be broken to render the hydrogel (and any coagulant) effective following implantation of the valve in a patient.

15 Claims, 3 Drawing Sheets

PROSTHETIC HEART VALVES

BACKGROUND OF THE INVENTION

This invention relates to prosthetic heart valves, and more particularly to enhancements to prosthetic heart valves that can reduce their possible thrombogenicity shortly after implantation.

Heart valve sewing cuffs are typically made of porous fabric. The fabric allows easy valve attachment to the patient's tissue, and the porosity-induced surface roughness encourages tissue ingrowth. After the healing is completed, the tissue-covered cuff is completely blood-compatible. However, during the healing process, the cuff may be thrombogenic and may therefore produce thromboembolism (TE). As a result, even patients who are receiving valves that normally do not need anticoagulation (e.g., tissue valves) still typically receive anticoagulation therapy for approximately three months after heart valve implantation.

In view of the foregoing, it is an object of this invention to reduce or eliminate the possible thrombogenicity of prosthetic heart valve sewing cuffs.

SUMMARY OF THE INVENTION

This and other objects of the invention are accomplished in accordance with the principles of the invention by including a hydrogel material in the sewing cuff of a prosthetic heart valve. The hydrogel material reduces the possibility of thromboembolism by chemically and/or physically improving the blood compatibility of the cuff. The hydrogel physically fills the pores of the cuffs and makes the cuff surface smoother. An anticoagulant can be bonded to the hydrogel to provide local anticoagulation at the valve cuff to prevent thromboembolism after valve implantation. A valve with such a cuff may not need systemic anticoagulation after surgery.

The two principal types of prosthetic heart valves are mechanical heart valves and tissue heart valves. Unlike mechanical heart valves, conventional tissue heart valves must be stored (prior to use) in a packaging solution. For tissue valve applications of the invention, the hydrogel (and the anticoagulant, if any) needs to be resistant to hydrolysis or other reaction with the packaging solution so that an acceptable shelf life can be achieved. In accordance with a possible further aspect of the invention, chemical interactions between the hydrogel and the packaging solution are prevented by enclosing the hydrogel in a pouch in the sewing cuff. During valve implantation, the pouch is punctured (e.g., by the needle when suturing the valve into the patient). This allows release of the gel and/or any associated anticoagulant into the surrounding sewing cuff fabric and/or tissue. Although use of such a pouch is particularly helpful in the case of tissue valves, this approach can also be employed with mechanical valves if desired.

Further features of the invention, its nature and various advantages, will be more apparent from the accompanying drawings and the following detailed description.

DETAILED DESCRIPTION

Figure 2:
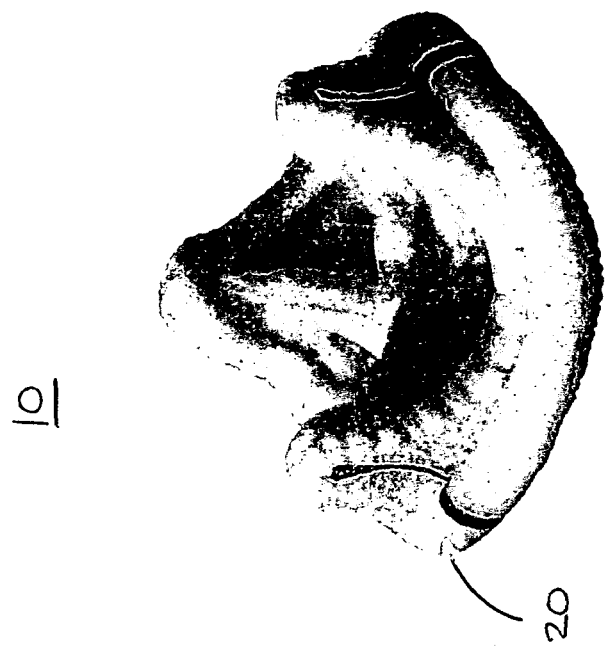
FIG. 2 is another view of the prosthetic heart valve of FIG. 1.
Figure 1:
FIG. 1 is a simplified elevational view of an illustrative prosthetic heart valve that can be constructed in accordance with the invention.

An illustrative prosthetic heart valve 10 that can be constructed in accordance with the invention is shown in FIGS. 1 and 2. Heart valve 10 is a tissue valve, but it will be understood that it could alternatively be a mechanical valve. One of the features of heart valve 10 is sewing cuff 20, which projects radially outwardly from the remainder of the valve, and which extends annularly around the outside of the valve. Sewing cuff 20 is typically used to suture the valve into the patient. In particular, a suture needle (not shown in FIGS. 1 and 2) is typically used to pass one or more strands of suture material (not shown) through sewing cuff 20 and adjacent tissue of the patient to hold the valve in place in the patient. Alternatively, other means of attachment such as staples, hooks, etc., may be used to attach sewing cuff 20 to adjacent tissue and thereby secure valve 10 in the patient.

At least the outer layer of sewing cuff 20 is typically a biocompatible, porous fabric such as knitted or woven dacron or teflon. Such fabric may also be used elsewhere on the outside of valve 10, and, indeed, at least the outer fabric of sewing cuff 20 may be integral with such other fabric on the outside of the valve.

In accordance with this invention, sewing cuff 20 includes a hydrogel material that can reduce the possibility of thromboembolism (TE) by chemically improving the blood compatibility of the cuff and physically filling the pores of the cuff fabric and making the cuff surface smoother. For example, the hydrogel can be applied to sewing cuff shortly prior to implanting valve 10 in a patient. More preferably, valve 10 is manufactured with the hydrogel material already in sewing cuff 20. In the case of a mechanical valve that is stored in a dry condition, for example, the hydrogel may be in the fabric and/or other structure of sewing cuff 20. Alternatively the hydrogel can be in a hydrated state in a protective but frangible structure in the sewing cuff. In the case of a tissue valve (e.g., like depicted valve 10) that is stored in a packaging solution, the hydrogel can either be (1) a hydrogel that is resistant to interaction with the packaging solution and therefore anywhere in the fabric and/or other structure of sewing cuff 20, or (2) in a protective but frangible structure in sewing cuff 20.

Figure 3:
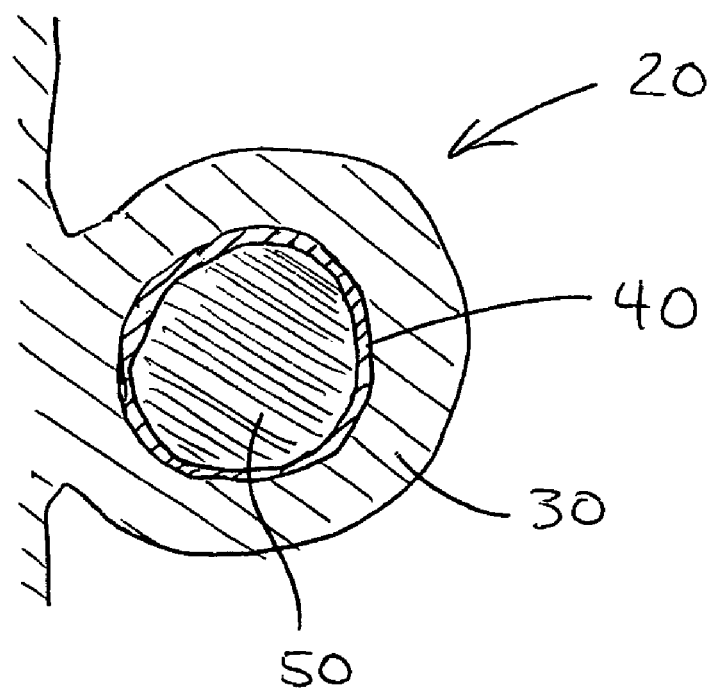
FIG. 3 is a simplified cross sectional view of an illustrative embodiment of a portion of a prosthetic heart valve in accordance with the invention.
Figure 4:
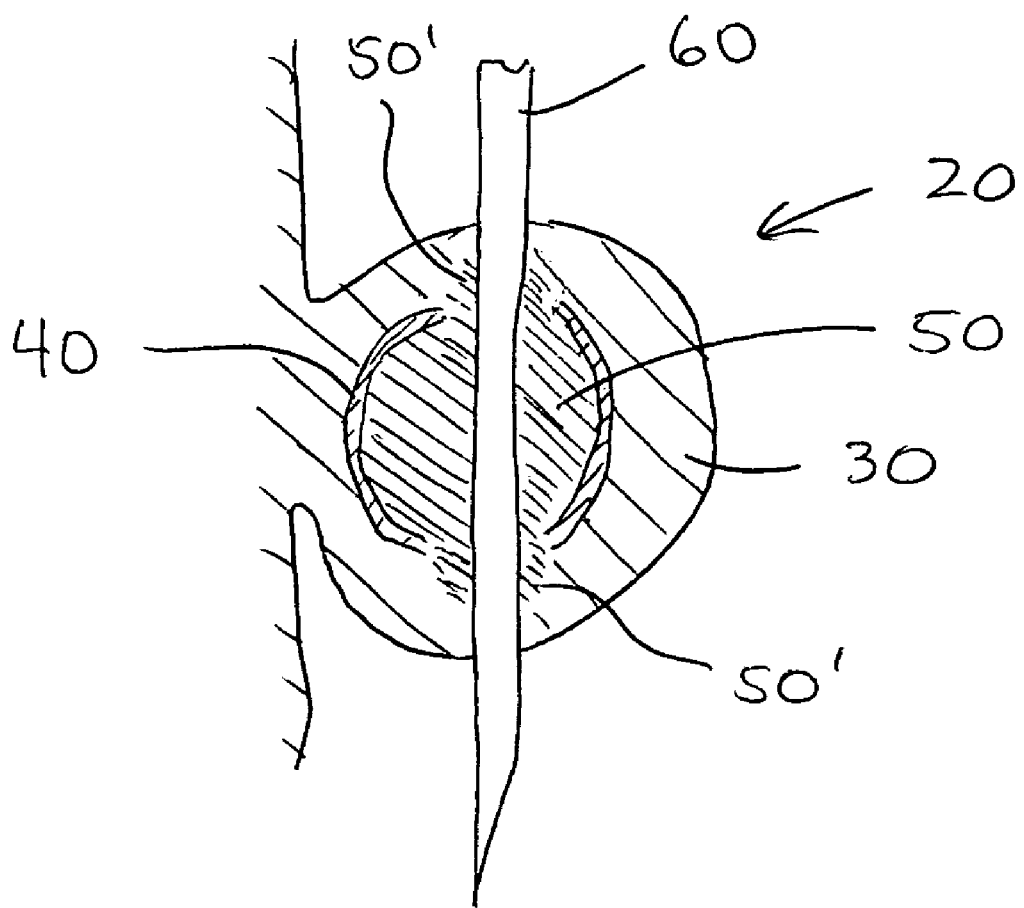
FIG. 4 is similar to FIG. 3 but shows the FIG. 3 structure at a later stage in its use in accordance with the invention.

FIGS. 3 and 4 illustrate the protective pouch possibility mentioned in the preceding paragraph. As shown in FIG. 3, hydrogel material 50 (in either a hydrated or a dehydrated form) is initially inside pouch 40. Pouch 40 is inside the outer fabric 30 of sewing cuff 20. Pouch 40 preferably extends annularly all the way around heart valve 10 inside sewing cuff 20. Preferred characteristics of pouch 40 include biocompatibility and water impermeability. Pouch 40 should also be resistant to whatever packaging solution (e.g., an aldehyde solution) that valve 10 maybe stored in. For example, pouch 40 may be made of a biocompatible, water impermeable polymer such as silicone or polyurethane. Pouch 40 is also preferably frangible with relative ease when it is desired to release hydrogel 50 from the pouch. For example, pouch 40 may preferably be made thin enough to be easily penetrated or punctured by a suture needle or other valve attachment means during valve implantation. This possibility is illustrated by FIG. 4 which shows suture needle 60 passing through pouch 40 and thereby creating breaks in pouch 40 that allow hydrogel 50 to leave the pouch and enter outer fabric 30 as indicated at areas 50. If desired, pouch 40 may be provided with areas of weakness to facilitate and/or otherwise promote its deliberate breakage (and consequent wide dispersal or exposure of hydrogel 50 to fabric 30 or other structure of cuff 20) shortly before or during implanting of valve 10.

Although pouch 40 is deliberately frangible as described above, all of the pieces of the debris of pouch 40 after it has been broken are preferably large enough to be permanently retained inside the other structure (e.g., outer fabric 30) of cuff 20.

The references herein to deliberate frangibility or the like mean that pouch 40 preferably maintains its integrity during normal handling of the valve until something is done to deliberately or intentionally break the pouch. Such deliberate breakage can be penetration of the pouch by a suture needle (e.g., as in FIG. 4) and/or any other handling that deliberately breaks, ruptures, or opens up the pouch.

A preference of the invention is for the hydrogel material to impregnate the outer fabric of sewing cuff 20, at least after implanting of the valve.

Another possibility (and, indeed, preference) for all embodiments of the invention is for the hydrogel material to include an anticoagulant such as heparin. The anticoagulant can be bonded to or otherwise loaded in the hydrogel to provide local anticoagulation at valve cuff 20 to prevent TE after valve implantation. There is preferably a slow release of the anticoagulant as the hydrogel slowly breaks down following implantation of the valve.

Examples of networks of hydrophilic polymers, i.e. hydrogels, include, but are not limited to, poly(ethylene oxide), poly(hydroxyethyl methacrylate), poly(vinyl alcohol), polyacrylamide, poly(vinylpyrrolidone), poly(ethyloxazoline), poly(propylene oxide), poloxamines, polyacrylamide, hydroxypropylmethacrylate (HPMA), carboxymethyl cellulose, hydroxyethyl cellulose, methylhydroxypropyl cellulose, polysucrose, hyaluronate, chondroitin sulphate, dextran, alginate, chitosan, gelatin, and derivatives, mixtures, and copolymers thereof.

It will be understood that the foregoing is only illustrative of the principles of the invention, and that various modifications can be made by those skilled in the art without departing from the scope and spirit of the invention. For example, the particular materials mentioned above are only illustrative, and other suitable materials can be used instead if desire.

The invention claimed is:

1. A prosthetic heart valve comprising:
   a sewing cuff; and
   a hydrogel material in the sewing cuff, wherein the sewing cuff comprises:
   a frangible pouch for initially holding the hydrogel material.

2. The prosthetic heart valve defined in claim 1 wherein the frangible pouch comprises:
   a biocompatible material.

3. The prosthetic heart valve defined in claim 1 wherein the frangible pouch comprises:
   a water impermeable material.

4. The prosthetic heart valve defined in claim 1 wherein the pouch is frangible by means used to implant the valve in a patient.

5. The prosthetic heart valve defined in claim 1 wherein the pouch is frangible by penetration with a suture needle.

6. The prosthetic heart valve defined in claim 1 wherein the sewing cuff further comprises:
   an outer layer of fabric.

7. The prosthetic heart valve defined in claim 6 wherein the pouch is disposed inside the outer layer of fabric.

8. The prosthetic heart valve defined in claim 7 wherein the outer layer of fabric extends annularly around the heart valve.

9. The prosthetic heart valve defined in claim 8 wherein the pouch extends annularly around the heart valve inside the outer layer of fabric.

10. The method of using a prosthetic heart valve comprising:
    breaking a pouch that contains a hydrogel, wherein the pouch forms part of a sewing cuff of the valve.

11. The method defined in claim 10 wherein the valve is stored, for a time prior to its implantation in a patient, in a packaging solution, and wherein the method further comprises:
    removing the valve from the packaging solution prior to the breaking of the hydrogel-containing pouch.

12. The method defined in claim 10 wherein the breaking comprises:
    puncturing the pouch by means used to implant the valve in a patient.

13. The method defined in claim 12 wherein the puncturing is a result of passing the means used to implant the valve through the sewing cuff in order to implant the valve in the patient.

14. The method defined in claim 10 wherein the breaking comprises:
    puncturing the pouch with a suture needle.

15. The method defined in claim 14 wherein the puncturing is a result of passing the suture needle through the sewing cuff in order to suture the valve into the patient.

* * * * *